(12) United States Patent
Pekin

(10) Patent No.: US 8,033,045 B2
(45) Date of Patent: Oct. 11, 2011

(54) LINE TENSION MEASURING DEVICE

(76) Inventor: David F. Pekin, San Diego, CA (US)

( * ) Notice: Subject to any disclaimer, the term of this patent is extended or adjusted under 35 U.S.C. 154(b) by 0 days.

(21) Appl. No.: 12/839,735

(22) Filed: Jul. 20, 2010

(65) Prior Publication Data

US 2011/0035985 A1 Feb. 17, 2011

Related U.S. Application Data

(60) Division of application No. 11/977,714, filed on Oct. 24, 2007, now Pat. No. 7,779,573, which is a continuation-in-part of application No. 11/307,840, filed on Feb. 24, 2006, now Pat. No. 7,318,295.

(51) Int. Cl.
*A01K 97/00* (2006.01)
(52) U.S. Cl. .............................................. 43/17; 43/22
(58) Field of Classification Search ................ 43/17, 22, 43/20, 18.1 R
See application file for complete search history.

(56) References Cited

U.S. PATENT DOCUMENTS

| | | | | |
|---|---|---|---|---|
| 3,315,401 A * | 4/1967 | Wagner | ............................. | 43/25 |
| 5,182,873 A * | 2/1993 | Aragon, Jr. | ....................... | 43/17 |
| 6,253,483 B1 * | 7/2001 | Reams | ............................... | 43/17 |
| 6,393,753 B1 * | 5/2002 | Walker | .............................. | 43/17 |
| 7,322,253 B2 * | 1/2008 | Owens | ..................... | 73/862.391 |
| 7,861,154 B2 * | 12/2010 | MacLaurin | .................... | 715/230 |
| 7,934,338 B2 * | 5/2011 | Hope | ................................ | 43/17 |
| 2010/0000143 A1 * | 1/2010 | Pekin | ................................ | 43/17 |

* cited by examiner

*Primary Examiner* — Christopher P Ellis
(74) *Attorney, Agent, or Firm* — Larry K. Roberts

(57) ABSTRACT

An exemplary embodiment of Ihe invention is a fishing reel seat including a reel mounting mechanism having a longitudinal axis configured for firmly attaching a fishing reel, and a reel mount receiving portion, wherein the reel mounting mechanism is configured to move in a substantially longitudinal direction with respect to the reel mount receiving portion in response to an externally generated force. The force measurement device includes a sensor configured to produce a response, in operational mode, indicative of the externally generated force based in the movement of the reel mounting mechanism with respect to the reel mount receiving portion.

5 Claims, 15 Drawing Sheets

LINE TENSION MEASURING DEVICE

CROSS-REFERENCE TO RELATED APPLICATIONS

This application is a division of U.S. application Ser. No. 11/977,714, filed Oct. 24, 2007, now U.S. Pat. No. 7,779,573 in turn a continuation-in-part of U.S. application Ser. No. 11/307,840, filed Feb. 24, 2006, now U.S. Pat. No. 7,318,295 to Pekin, the entire contents of which are incorporated herein by this reference.

The invention is a fishing pole with an integrated line tension measuring device. Measuring fishing line tension or "drag" has always been subjective. Most often a fisherman pulls on the line by hand and adjusts the drag, or braking force on the reel, based on what the pull 'feels' like. While fighting a fish, it is difficult to know how hard the fish is pulling on the line. The invention, a fishing pole that measures and displays the actual pull on the line in quantitative units, e.g. pounds or kilograms, enables the fisherman to accurately set the drag and know how hard a fish is pulling on the line. The line tension is measured and displayed continuously, thereby enabling the fisherman to accurately adjust the drag even when fighting a fish.

FIELD OF INVENTION

This invention applies to the field of fishing and more particularly to the design of fishing poles.

DISCUSSION OF PRIOR ART

In the field of sport fishing, the desire for a proper drag setting is a continuing, yet unsatisfied goal. Current fishing reels apply a drag, or braking force, to the line by a variety of mechanisms. In an effort to measure the drag or braking force on the line, a variety of apparatus have been disclosed. For example, U.S. Pat. No. 960,535 Gilfillan, Jun. 7, 1910; U.S. Pat. No. 2,603,474, Mandolf, Jul. 15, 1952; and U.S. Pat. No. 4,660,666; Reder, Apr. 28, 1987, disclose fishing scales and weights that are equipped with hooks to attach to a reel to be adjusted. In the practical environment, however, fishermen prefer to keep their fishing line threaded through the "eyes" of their fishing rods with a lure or hook tied at the end of the line. A rod and reel set maintained in this form is termed "rigged." To measure the drag on a rigged rod and reel using the aforementioned systems, the hook would either have to be attached at the lure, or to a loop tied on the fishing line between the reel and the first eye of the rod. In the first method, setting the drag would require one person to hold the scale, while a second person holds the reel to monitor the drag release. While the second method can be performed by a single person by attaching the scale to the loop, this would require re-threading the line through the eyes of the rod and retying the lure each time that a drag measurement is performed. Both approaches are impractical and not used by the average fisherman.

U.S. Pat. No. 6,339,198 issued to Yamanouchi, Jan. 15, 2002 discloses a hand held scale to measure line drag by threading the line through a pulley and pulling the scale apparatus away from the reel until the drag slips. This approach is difficult and requires the fisherman to carry this extra apparatus with him.

U.S. Pat. No. 5,639,038 issued to Hirose Jun. 17, 1997 discloses a fishing reel with a mechanism for measuring line tension. This device employs a coil opposed to thin magnetostrictive bands bonded to the spool shaft to determine the torque applied to the spool shaft. In order to translate torque into line tension, the height of the line wound onto the spool must be determined with, for example, an ultrasonic measuring device. While this device may actually produce a quantifiable measurement, the circuitry involved is relatively complex and would be correspondingly expensive. Fishing reels are already one of the more significant expenses in fishing and purchasing new reels with this type of mechanism would be very expensive. The present invention described herein allows significant cost savings versus a reel based measurement system. The present invention allows the fisherman to use any existing fishing reel. Often times a fisherman will use a single pole with a variety of different reels, depending on the species of fish he is targeting.

U.S. Pat. No. 4,422,258 issued to Adams, et al. Dec. 27, 1983 discloses a device for measuring and signaling of fishing line pull which can be attached to a fishing pole. This device does not measure the line pull in quantitative units, but displays various color lights to indicate the amount of pull. This device requires the fishing line to be internally threaded through it for the line to press against the spring biased rod which switches the lights. Those skilled in the art realize that threading the fishing line through any device adversely impacts its practical application for fishing. For most types of fishing, the fishing line must run free from the reel through the fishing pole guides with no obstruction. Any additional routing of the fishing line through measuring apparatus will adversely impact both casting, where the line must run free and unimpeded from the reel, and fishing, where the fisherman needs the line sensitivity to feel the bait swimming and the target fish biting.

In spite of the aforementioned patents and devices, incorporated herein by reference, drag setting is still a practice normally performed prior to fishing by pulling the line by hand and setting the fishing reel drag to what 'feels' right. The present invention will change this and provide the user with accurate feedback in quantitative units, pounds or kilograms, to assist in accurately set the drag.

Reporting actual fishing line tension is important because current fishing reels do not apply constant fishing line tension. Fishing reel drags apply a near constant braking torque on the fishing line spool. The actual line tension applied by the drag varies due to a variety of factors however. It is readily apparent to those skilled in the art, that the actual line tension applied by the drag is dependent on the distance from the center of the spool to the outside of the fishing line winding. Therefore, the drag applied tension on the line varies relative to the amount of line on the spool. Additionally, the amount of drag applied by a reel may change as the drag mechanism heats or cools or binds.

Once a fisherman is engaged on a fish, the line tension varies due to the factors discussed in the previous paragraph. It is currently impossible to know the actual line tension when fighting a fish. It is also impossible to know accurately how the line tension changes when adjusting the drag while fighting a fish.

SUMMARY OF THE INVENTION

Accordingly, the present invention, a fishing pole with integrated line tension measuring device, measures the fishing line tension at all times without any ancillary apparatus. The invention provides the constant measurement and display of fishing line tension in quantitative units, e.g. pounds or kilograms. Using the invention, the user can monitor the fishing line tension applied by the drag precisely both before fishing, and more importantly, while a fish is being fought.

The invention allows the fisherman to adjust the drag and view the resulting line tension change immediately.

Further features and advantages of the invention will become apparent from the following detailed description and accompanying drawings which set forth illustrative embodiments in which the principles of the invention are described.

BRIEF DESCRIPTION OF DRAWINGS

These and other objects, features and advantages of the invention will become more apparent upon reading the following detailed specification and drawings, in which.

DETAILED DESCRIPTION OF THE PREFERRED EMBODIMENTS

Figure 1:
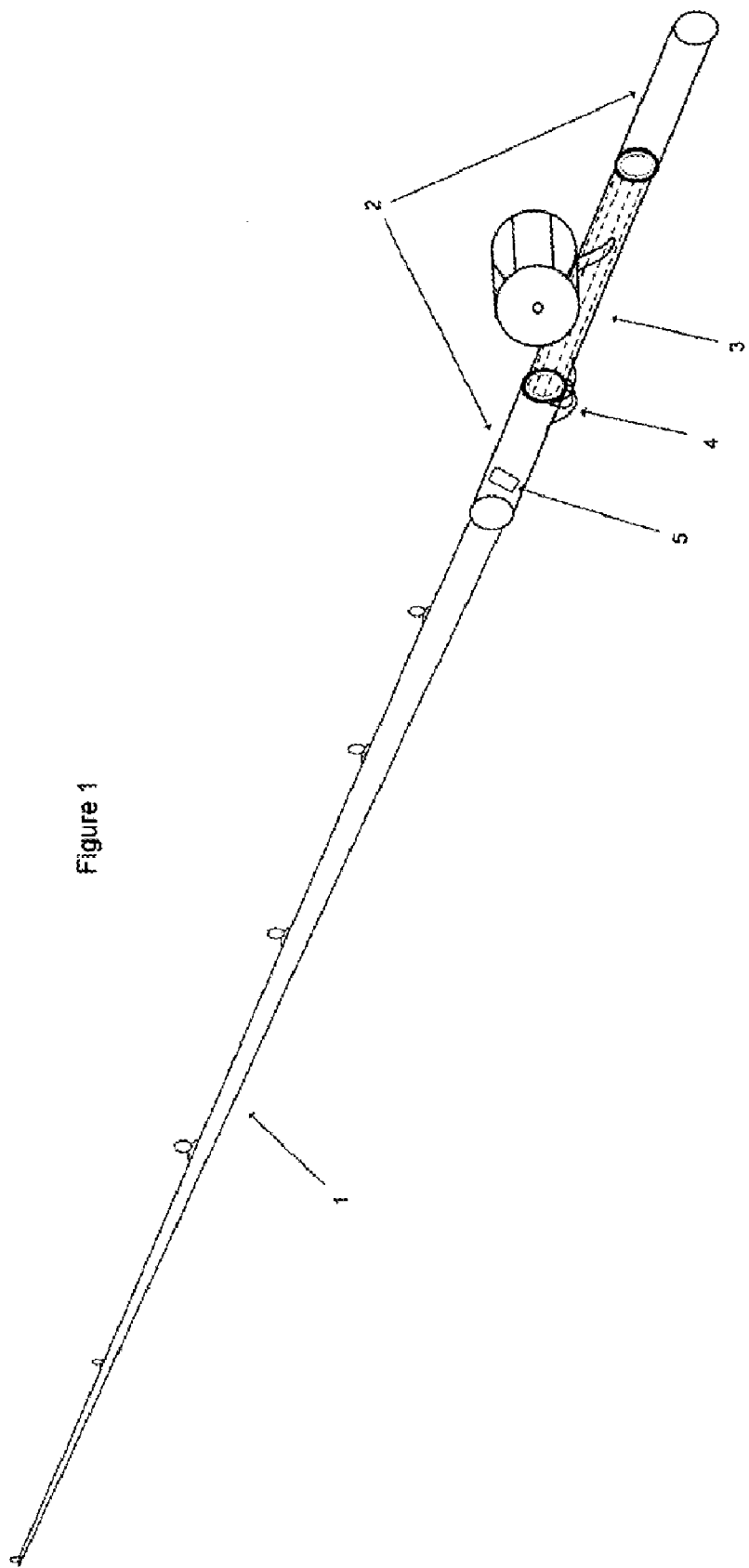
FIG. 1 is a perspective view showing a first embodiment of the fishing pole with integrated line tension measuring device according to the invention.

Many of the figures describing the preferred embodiments of the inventions show a fishing reel for illustrative purposes. The fishing reel itself is not part of the invention. FIG. 1 is a perspective view showing the preferred embodiment of the fishing pole with integrated line tension measuring device according to the invention. A fishing pole consists of a rod (1) and handle (2). The rod extends all the way through the center of the handle to the base of the fishing pole. A reel seat (3), or place to connect the reel, is commonly situated in the center section of the handle. In this embodiment, the line tension measuring device (4) and line tension display (5) are integrated into the handle portion of the fishing pole.

Figure 2:
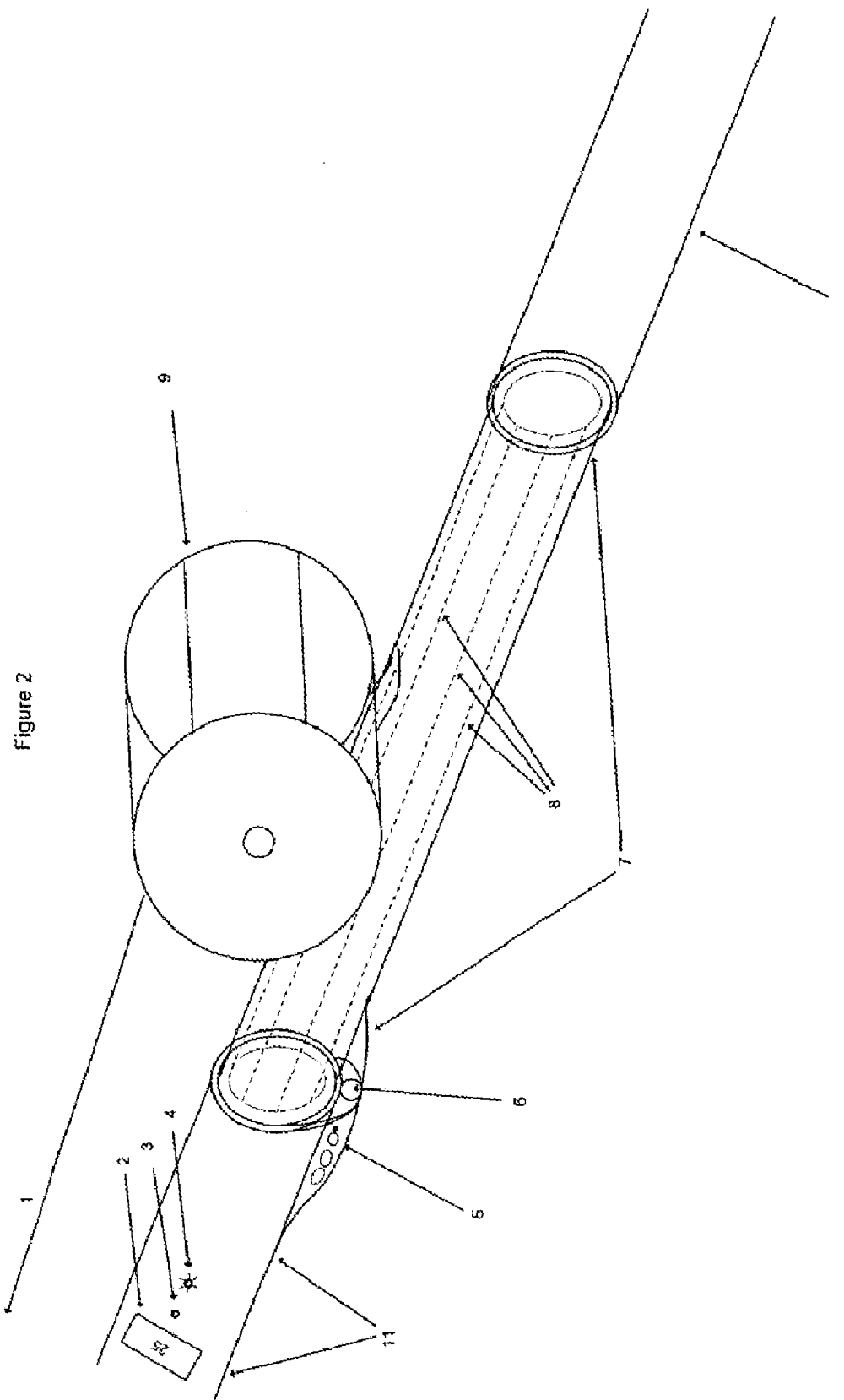
FIG. 2 is a view of the same embodiment detailing the fishing pole handle with integrated line tension measuring device.

FIG. 2 is a perspective view detailing the handle portion of the preferred embodiment of the fishing pole with integrated line tension measuring device according to the invention. The handle consist of the forward grip (11), a sliding reel mount (7), and the butt (10). The reel (9) is connected to the sliding reel mount (7) in the standard fashion. The reel (9) is solidly affixed to the sliding reel mount (7) and together act and move as a single unit. The sliding reel mount (7) is mounted on an internal spline or slide (8) which allows the reel/reel mount body (7,9) to move in the longitudinal direction along the long axis of the pole. The length of travel is very small and will be barely noticeable by the user. Rotation is prevented by the internal spline or slide (8). The sliding reel mount (7) contacts the pressure sensor (6) which measures the force applied by the fishing line (1). The fishing line (1) pulls the reel (9) and sliding reel mount (7) into the pressure sensor (6). The signal from the pressure sensor (6) drives the line tension display device (2) through the electronics package (5). Since the fishing line (1) pulls parallel to the internal spline or slide (8), the force applied on the pressure sensor (6) is essentially equivalent to the force exerted by the fishing line (1) and reel drag mechanism. FIG. 2 shows a visual line tension warning device (3) and an audible line tension warning device (4) placed in the forward grip (11). These devices warn the user when the line tension exceeds the line tension threshold as set by the user.

Figure 3:
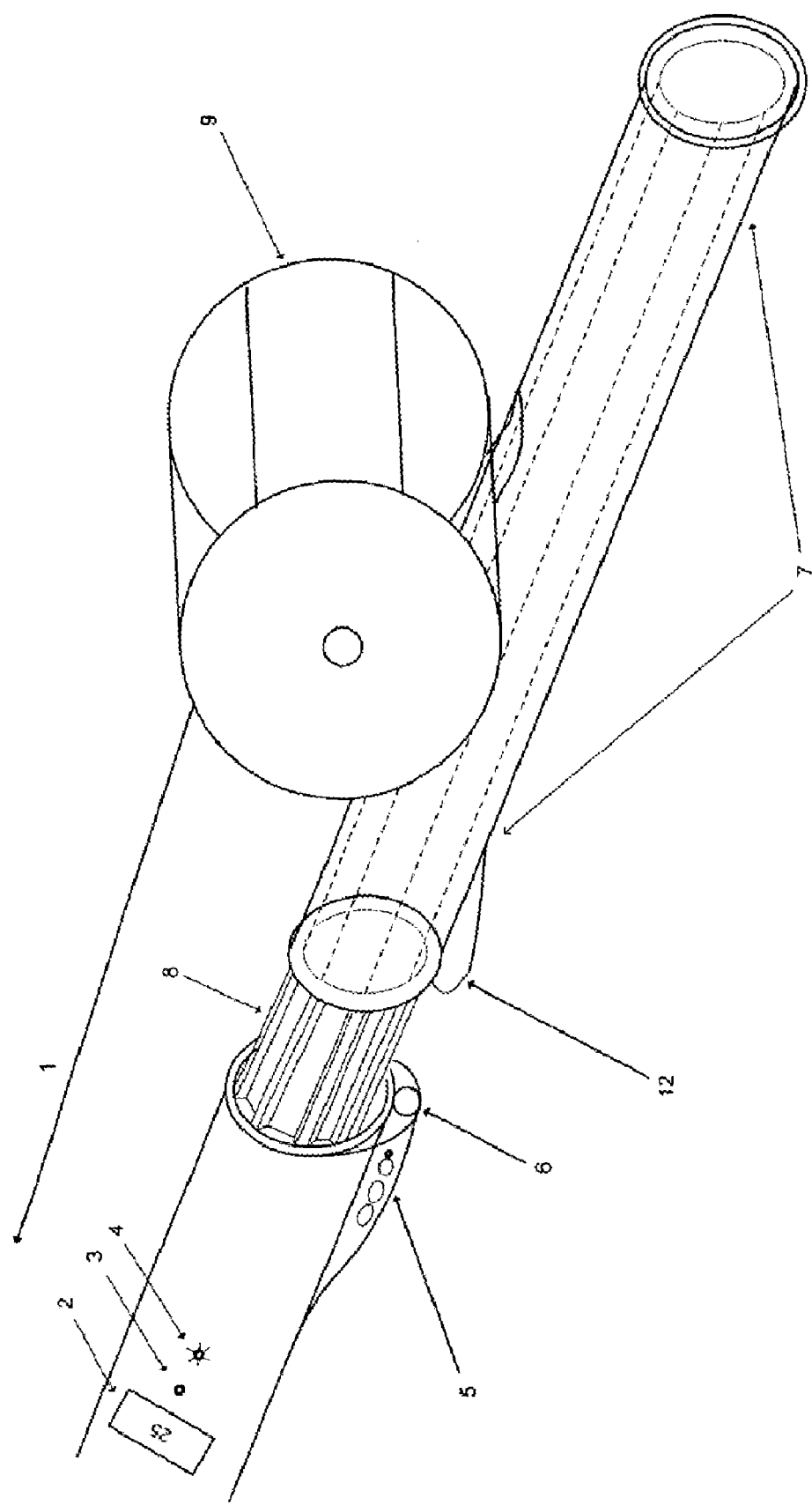
FIG. 3 is a view of the same embodiment detailing the sliding reel mount mechanism that applies the line tension pressure to the measurement device.

FIG. 3 is a perspective view detailing the internal construction of the preferred embodiment of the fishing pole with integrated line tension measuring device according to the invention. The numbering of the individual parts are the same as in FIG. 2. FIG. 3 depicts the fishing pole handle with the butt (10 in FIG. 2) removed. The sliding reel seat (7) slides on the internal spline or slide (8). The sliding reel seat (7) has a contact point (12) which applies pressure to the pressure sensor (6) when the handle is in its normal configuration.

Figure 4:
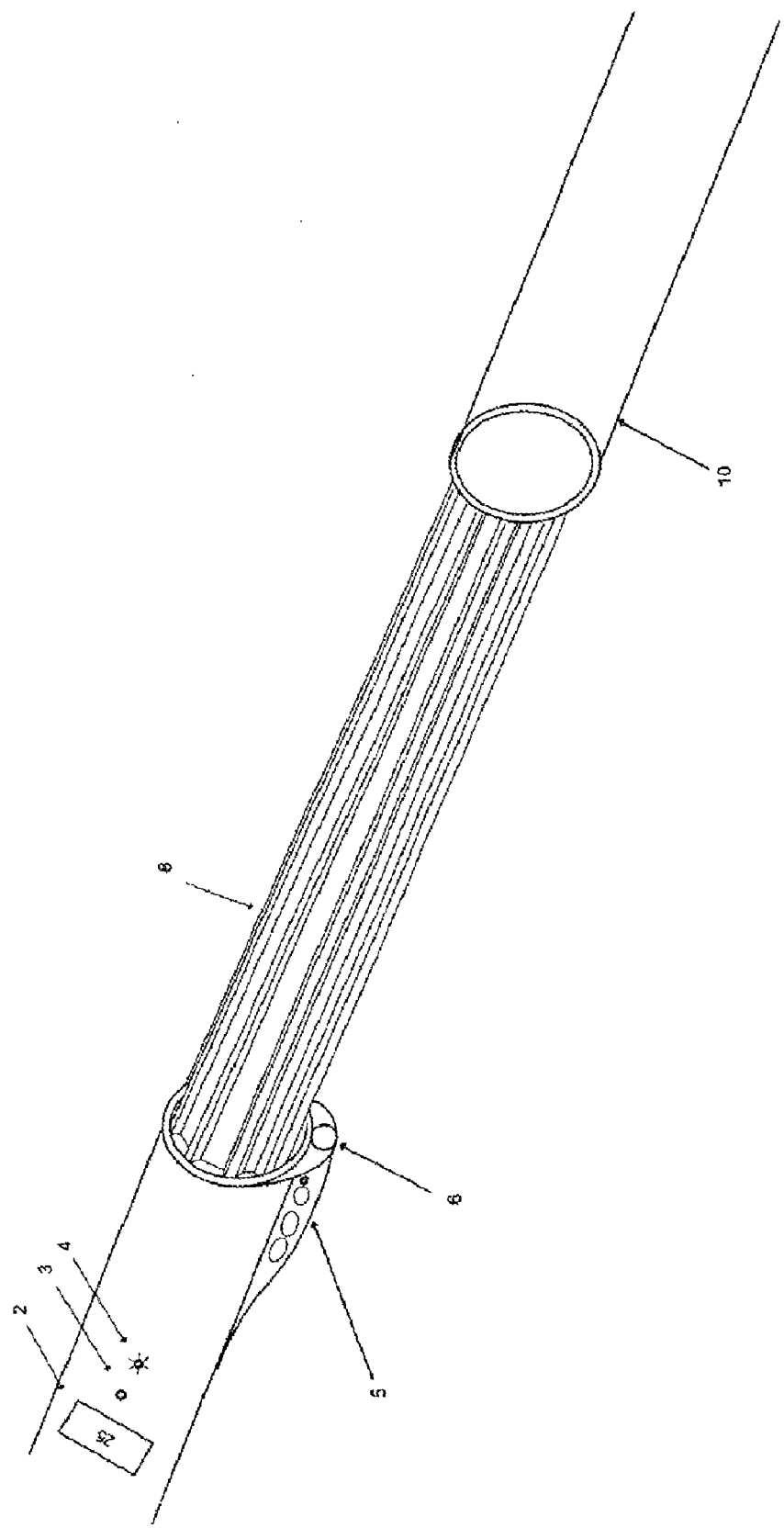
FIG. 4 is a view of the same embodiment with the sliding reel mount removed to show the internal slide apparatus.

FIG. 4 is a perspective view detailing the internal construction of the preferred embodiment of the fishing pole with integrated line tension measuring device according to the invention. The numbering of the individual parts are the same as in FIG. 2. FIG. 4 shows the fishing pole handle with the sliding reel seat and reel (7 & 9 in FIG. 2) removed for clarity.

Figure 5:
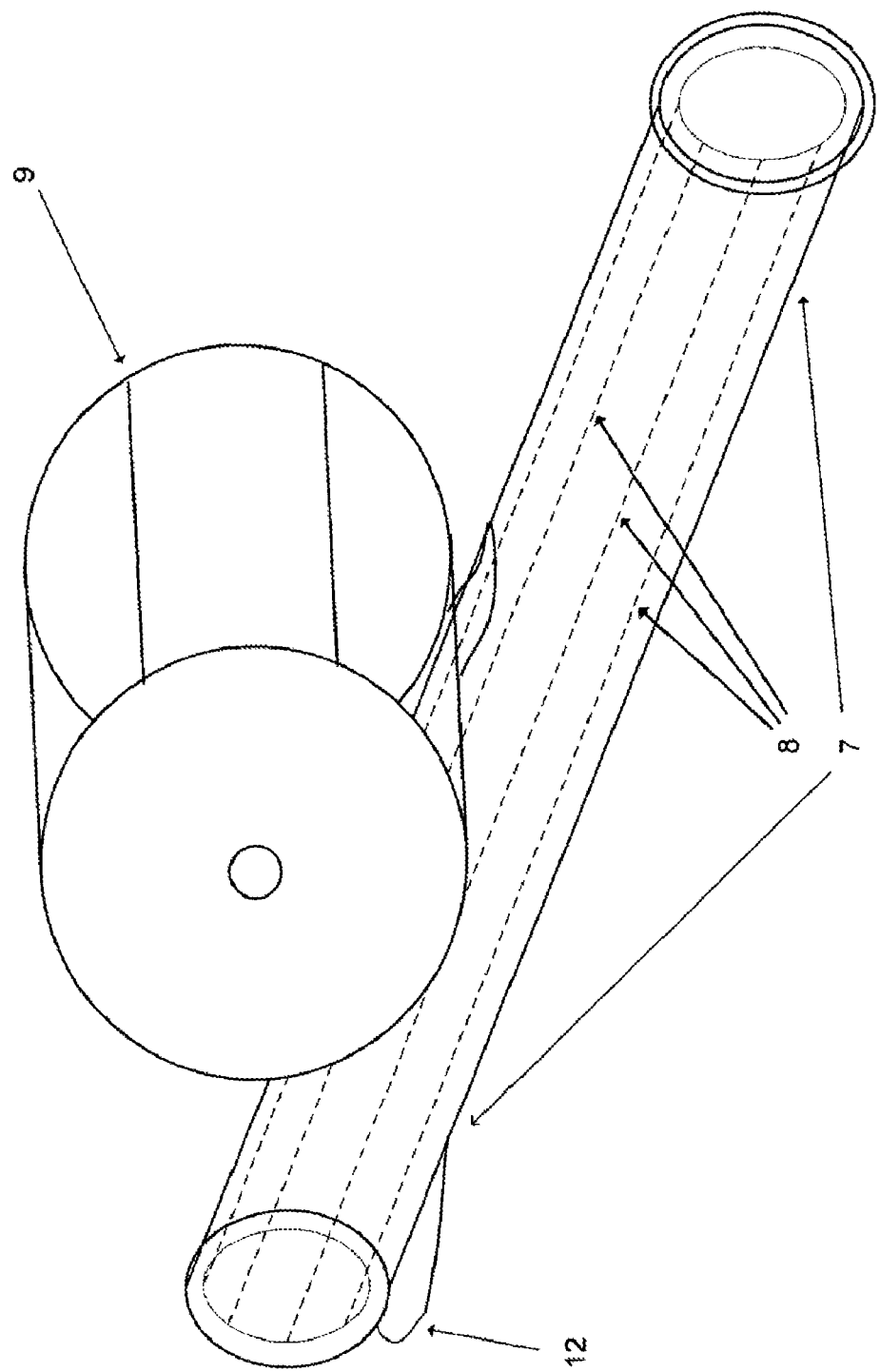
FIG. 5 is a view of the same embodiment detailing the sliding reel mount removed from the slide.

FIG. 5 is a perspective view detailing the construction of the preferred embodiment of the fishing pole with integrated line tension measuring device according to the invention. The numbering of the individual parts are the same as in FIG. 2. FIG. 5 shows the sliding reel mount and reel (7 & 9). The internal spline or slide (8) allows the sliding reel mount (7) contact point (12) to apply pressure on the pressure sensor (6 in FIG. 2). For clarity, the reel clamps on the sliding reel mount have not been shown. They are of the standard twist lock type, well known to those skilled in the art. The actual method of attaching the reel to the sliding reel mount is not material to the invention.

Figure 6:
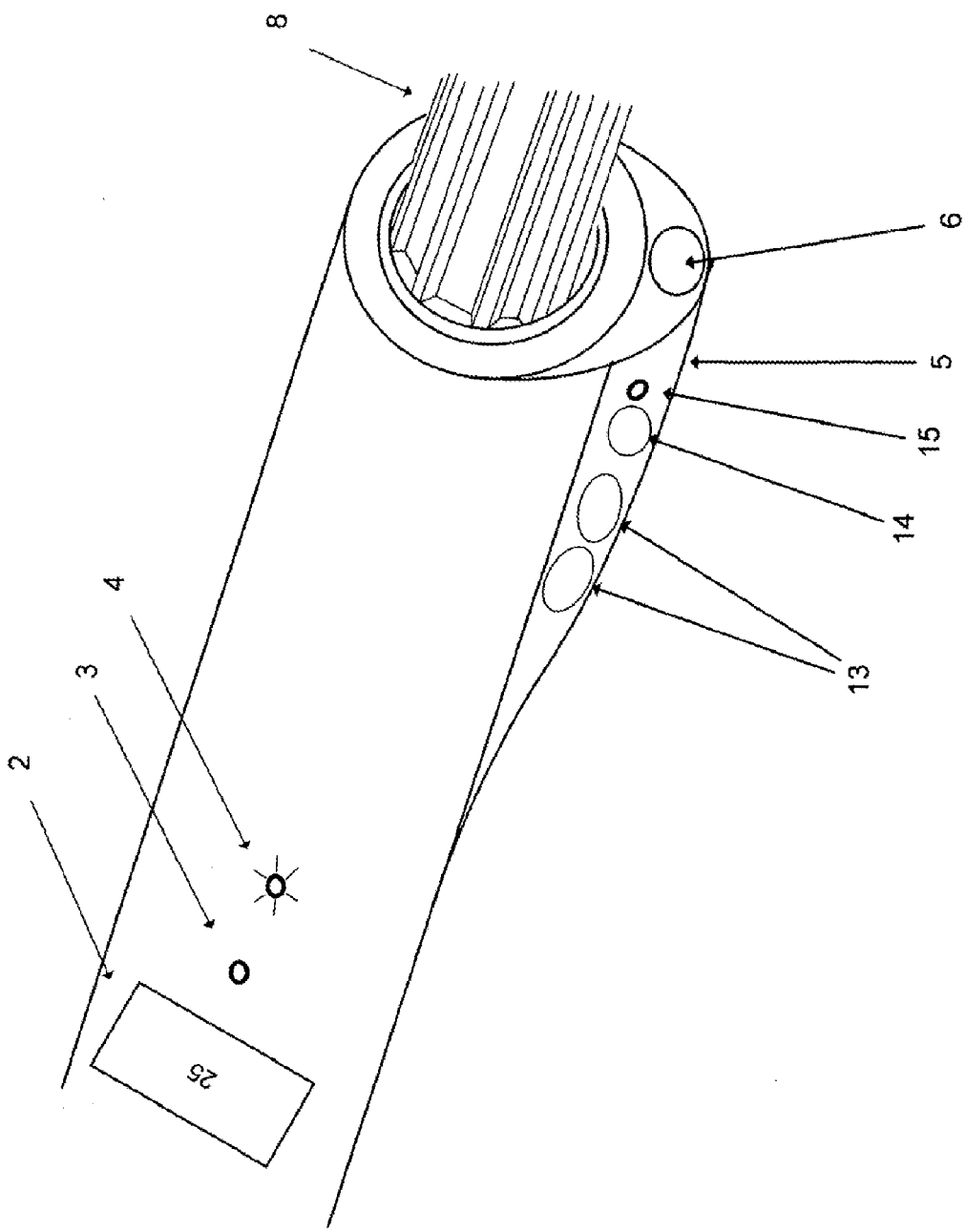
FIG. 6 is a view of the same embodiment detailing the display, warning devices, and electronics package in the handle of the fishing pole.

FIG. 6 is a perspective view detailing the electronics package of the preferred embodiment of the fishing pole with integrated line tension measuring device according to the invention. The electronics package contains the control buttons (13), battery cover (14), and data jack (15). The actual electronics are inside the electronics package and not shown. The batteries (internal, not shown) supply the power to the pressure sensor (6), electronics (internal, not shown), display (2) and warnings (3,4). In this embodiment, the line tension display (2) is a liquid crystal display commonly called an LCD. The line tension visual warning (3) is a light emitting diode commonly called an LED. The line tension audible warning (4) is a piezo buzzer. The data jack (15) allows the connection of other electronic equipment to the pressure sensor output. In this embodiment, the data jack (15) provides an analog voltage output proportional to the pressure applied to the pressure sensor (6).

The control buttons (13) control the modes of operation of the display (2) and warning indicators (3,4). The modes of operation of the preferred embodiment are: Setup, real-time tension, maximum tension, and threshold sensing.

Setup mode controls the display and warning parameters. The display (2) can be configured to show pounds or kilograms. Setup allows the user to specify a line tension threshold in the selected units. Setup allows the user to activate or de-activate the line tension threshold alarms.

Real-time mode displays the current line tension on the display (2) in the selected units, pounds or kilograms.

Maximum tension mode holds and displays the maximum tension in the selected units. Pressing either control button while in maximum tension mode resets the maximum tension hold register to 0. Maximum tension mode would be used to set the drag on the fishing reel. The user would pull the line from the reel until the reel drag slipped. The display would show the maximum amount of line tension applied by the reel drag.

Threshold sensing mode monitors the line tension and activates the audible (4) and visual (3) warnings if the measured line tension exceeds the set threshold. Pressing either control button when the alarms are activated turns off the alarms. Threshold sensing could be used to detect fish biting, or detect fouling of lures or hooks while fishing or trolling.

Figure 7:
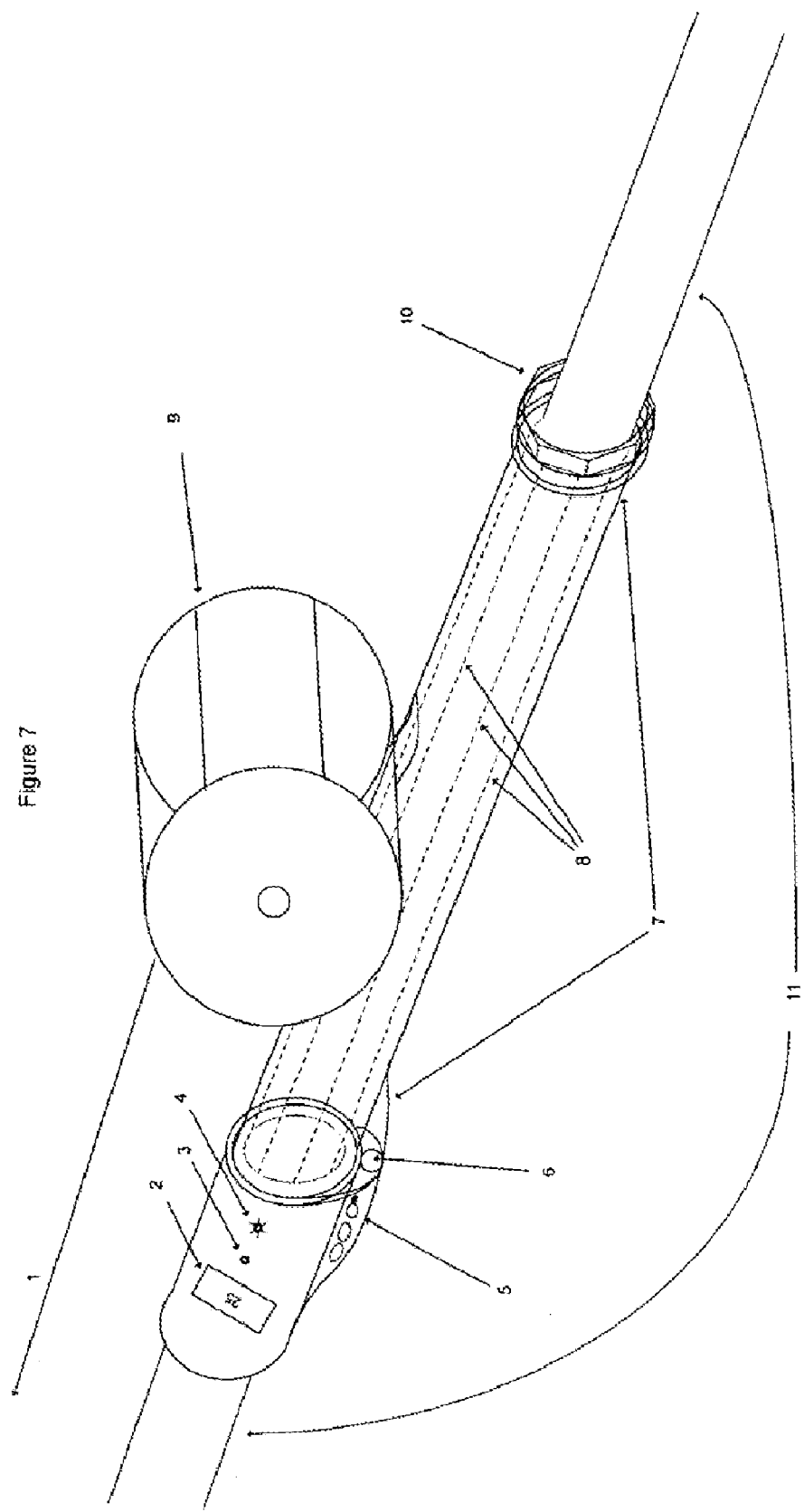
FIG. 7 is a perspective view showing a first embodiment of a reel seat with integrated line tension measuring device according to the invention.

FIG. 7 is a perspective view showing the preferred embodiment of a reel seat with integrated line tension measuring device according to the invention. Integrating the measuring device into a self contained reel seat mechanism reduces the complexity of building a fishing pole with an integrated line tension measuring device. During fabrication of fishing poles, the reel seat is slid onto the fishing rod blank and permanently affixed to the handle end of the rod. The complete reel seat mechanism as depicted in FIG. 7 can be fixed to the blank in the identical fashion, thereby simplifying production of a fishing pole with integrated line tension measuring device. In FIG. 7 the reel seat with integrated line tension measuring device is shown on the rod blank (11). The reel seat consist of a sliding reel mount (7), pressure sensor (6), electronics (5), line tension display and warnings (2,3,4), internal spline or slide (8), and lock nut (10) at the end of the spline or slide. The lock nut (10) controls the length of travel for the sliding reel mount (7). The lock nut (10) is adjusted to keep the reel mount (7) very close to the pressure sensor (6). The reel (9) is connected to the sliding reel mount (7) in the standard fashion. The reel (9) is solidly affixed to the sliding reel mount (7) and they move together as a single unit. The sliding reel mount (7) is mounted on an internal spline or slide (8) which allows the reel/reel mount body (7,9) to move in the longitudinal direction along the long axis of the pole. Rotation is prevented by the internal spline or slide (8). The sliding reel mount (7) contacts the pressure sensor (6) which measures the force applied by the fishing line (1). The fishing line (1) pulls the reel (9) and sliding reel mount (7) into the pressure sensor (6). The signal from the pressure sensor (6) drives the line tension display device (2) through the electronics package (5). Since the fishing line (1) pulls parallel to the internal spline or slide (8), the force applied on the pressure sensor (6) is essentially equivalent to the force on the fishing line (1).

Figure 8:
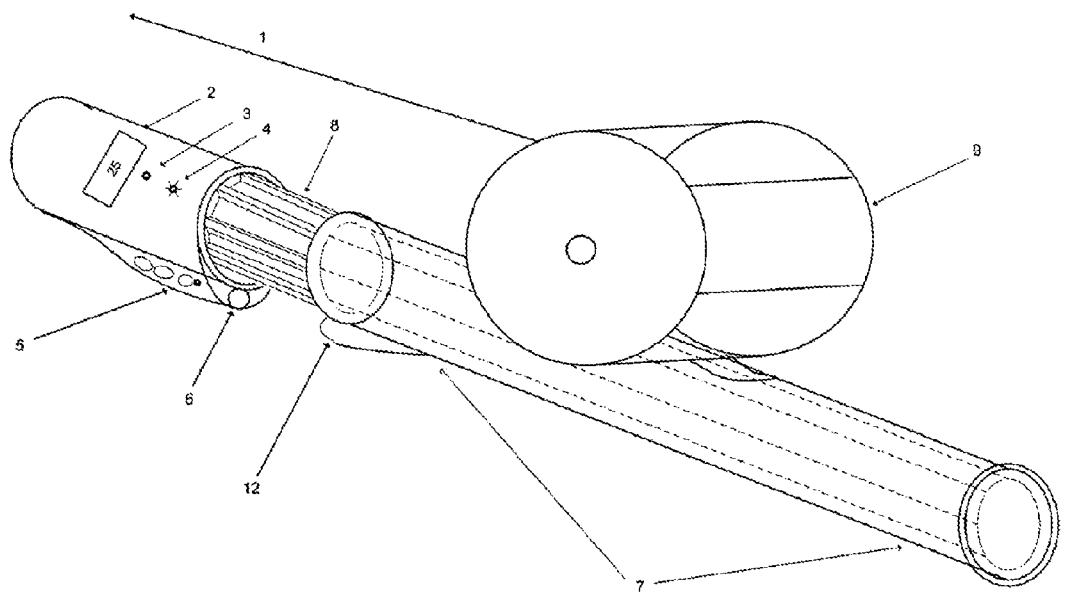
FIG. 8 is a view of the reel seat embodiment detailing the sliding reel mount mechanism that applies the line tension pressure to the measurement device.

FIG. 8 is a perspective view detailing the internal construction of the preferred embodiment of the reel seat with integrated line tension measuring device according to the invention. The numbering of the individual parts are the same as in FIG. 7. FIG. 8 depicts the reel seat with the lock nut (10 in FIG. 7) removed and the sliding reel mount (7) partially pulled down the internal spline or slide (8). The sliding reel mount (7) has a contact point (12) which applies pressure to the pressure sensor (6) when the sliding reel mount (7) is in its normal configuration.

Figure 9:
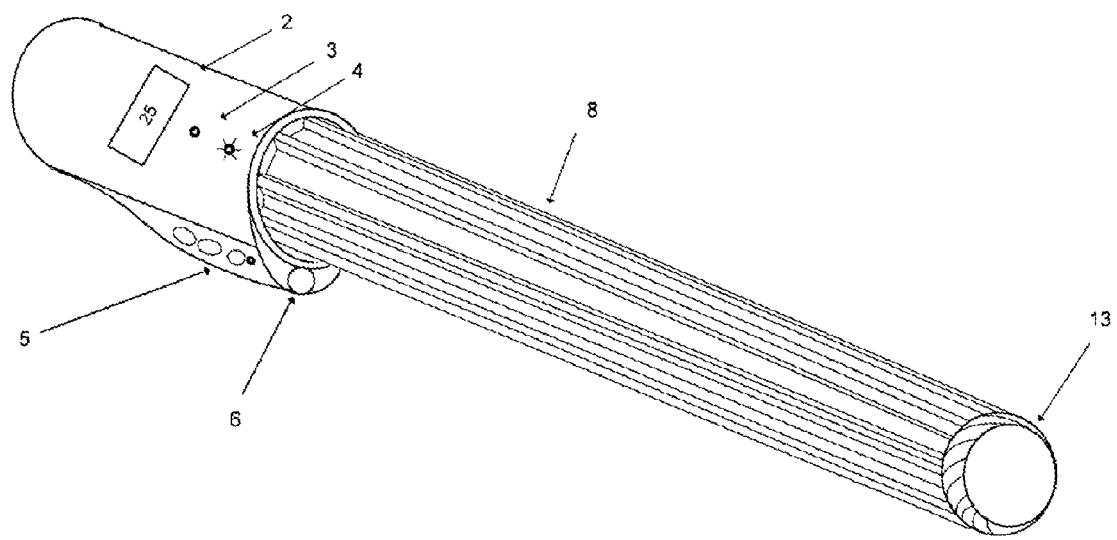
FIG. 9 is a view of the reel seat embodiment with the sliding reel mount mechanism removed to show the internal slide apparatus.

FIG. 9 is a perspective view detailing the internal construction of the preferred embodiment of the reel seat with integrated line tension measuring device according to the invention. The numbering of the individual parts are the same as in FIG. 8. FIG. 9 shows the reel seat with the sliding reel mount and reel (7 & 9 in FIG. 8) removed for clarity. FIG. 9 shows the threading (13) for the lock nut (10 in FIG. 7) at the end of the internal spline or slide (8). In normal configuration the lock nut limits the sliding reel mount travel and maintains a tight fit between the sliding reel mount and the pressure sensor.

Figure 10:
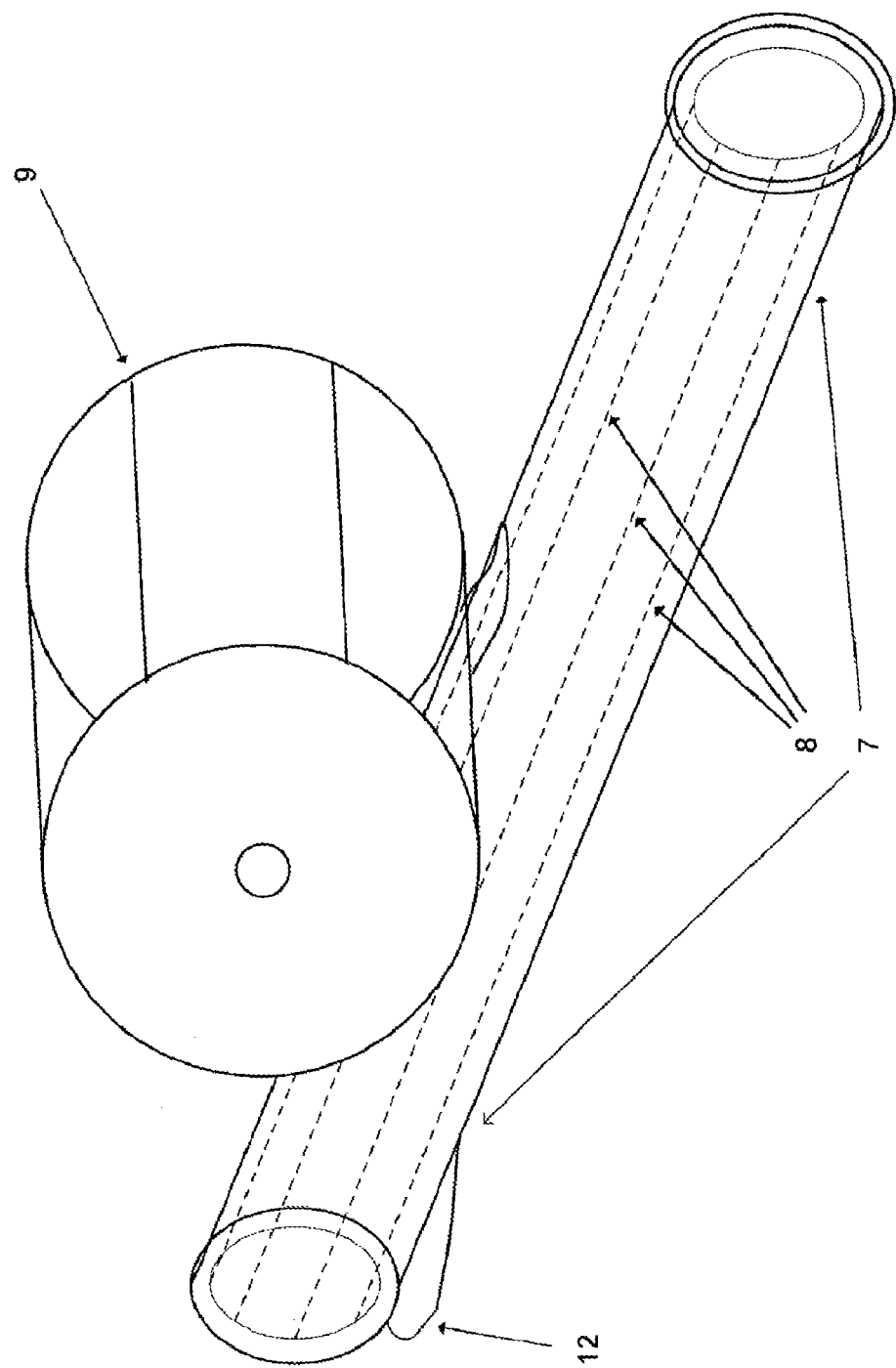
FIG. 10 is a view of the reel seat embodiment detailing the sliding reel mount removed from the reel seat.

FIG. 10 is a perspective view detailing the sliding reel mount and reel (7 & 9). The internal spline or slide (8) allows the sliding reel mount (7) contact point (12) to contact the pressure sensor (6 in FIG. 8). For clarity, the reel clamps on the sliding reel mount have not been shown. They are of the standard twist lock type, well known to those skilled in the art. The actual method of attaching the reel to the sliding reel mount is not material to the invention.

Figure 11:
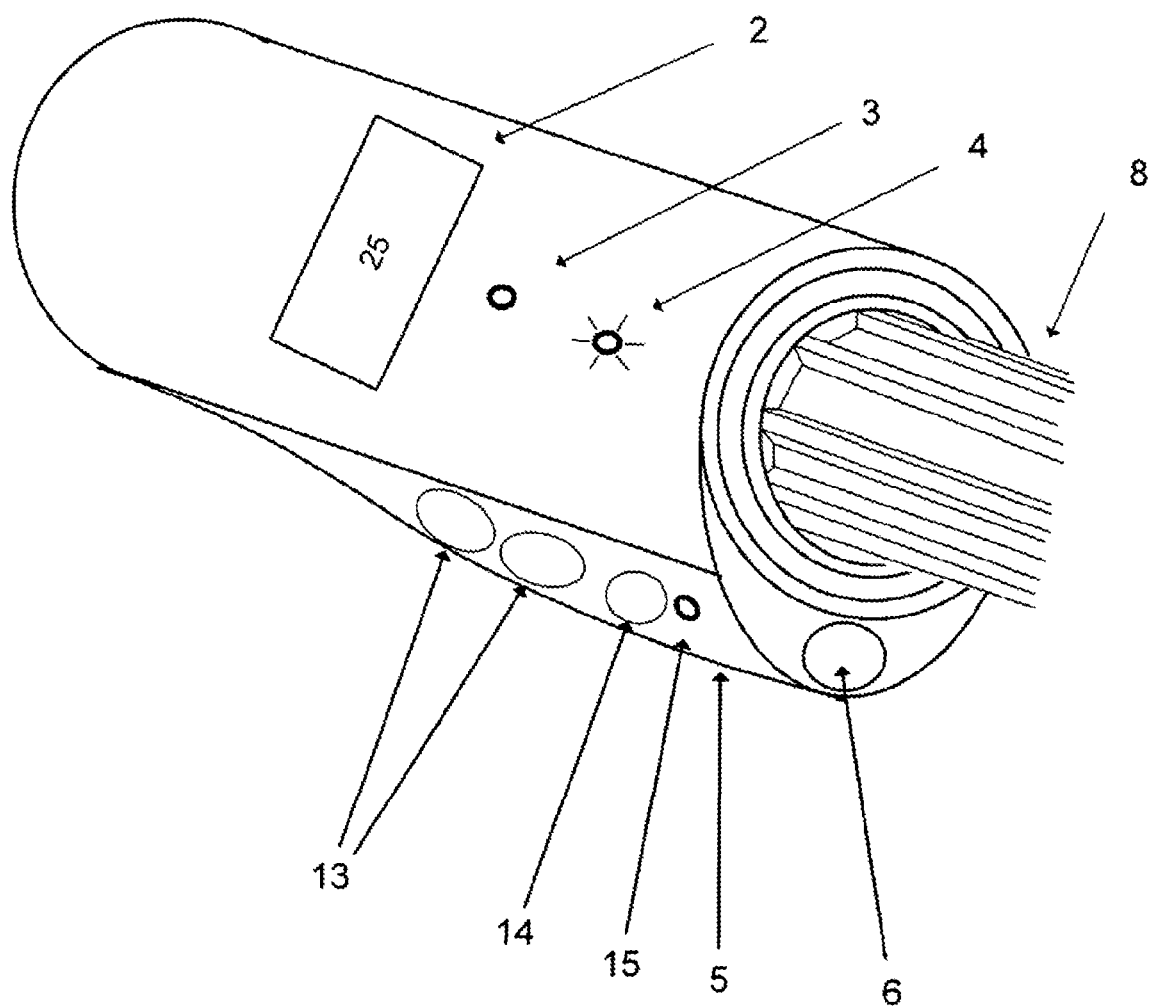
FIG. 11 is a view of the reel seat embodiment detailing the electronics package integrated in the reel seat.

FIG. 11 is a perspective view detailing the electronics package and display of the preferred embodiment of the reel seat with integrated line tension measuring device according to the invention. The numbering of the individual parts are the same as in FIG. 7. The electronics package (5 in FIG. 7) contains the control buttons (13), battery cover (14), and data jack (15). The actual electronics are inside the electronics package and not shown. The batteries (internal, not shown) supply the power to the pressure sensor (6), electronics, display (2) and warnings (3,4). In this embodiment, the line tension display (2) is a liquid crystal display commonly called an LCD. The line tension visual warning (3) is a light emitting diode commonly called an LED. The line tension audible warning (4) is a piezo buzzer. The data jack (15) allows the connection of other electronic recording equipment to the pressure sensor output. In this embodiment, the data jack (15) provides an analog voltage output proportional to the pressure applied to the pressure sensor (6). Operation of the buttons, alarms and display are as described above.

Figure 12:
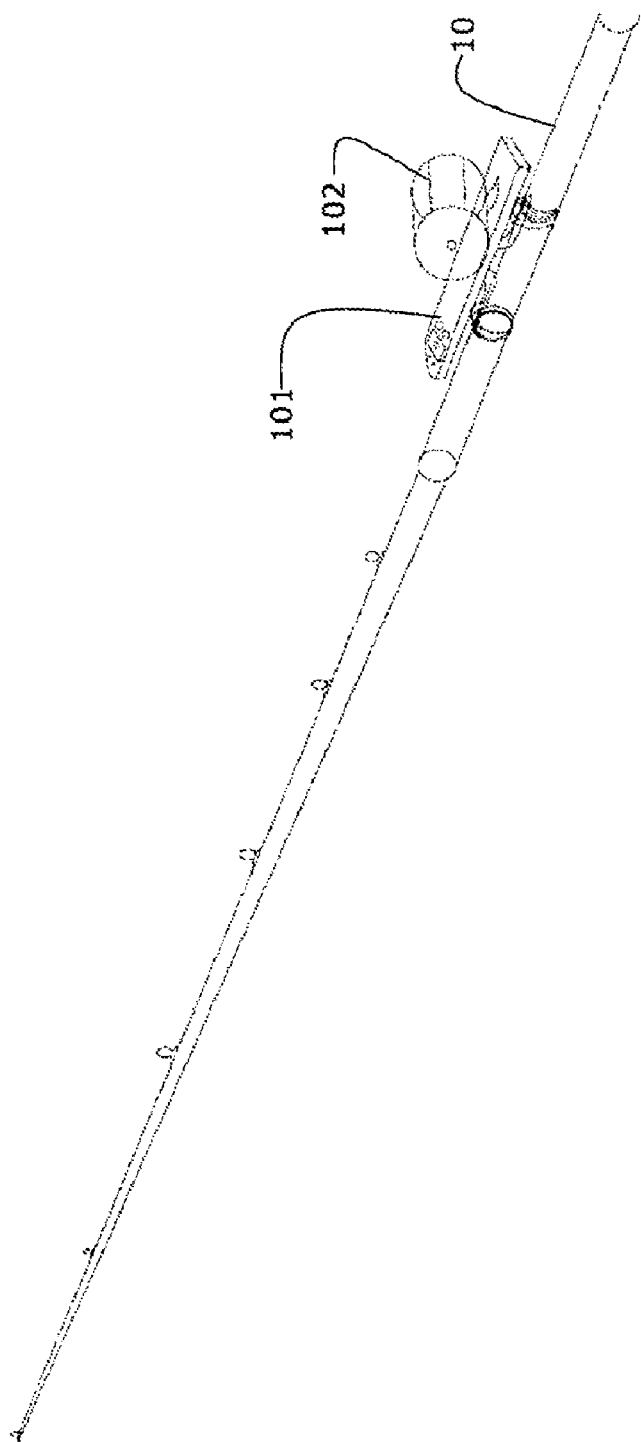
FIG. 12 is a perspective view of a reel and pole with a translation stage according to some embodiments of the present invention.
Figure 13:
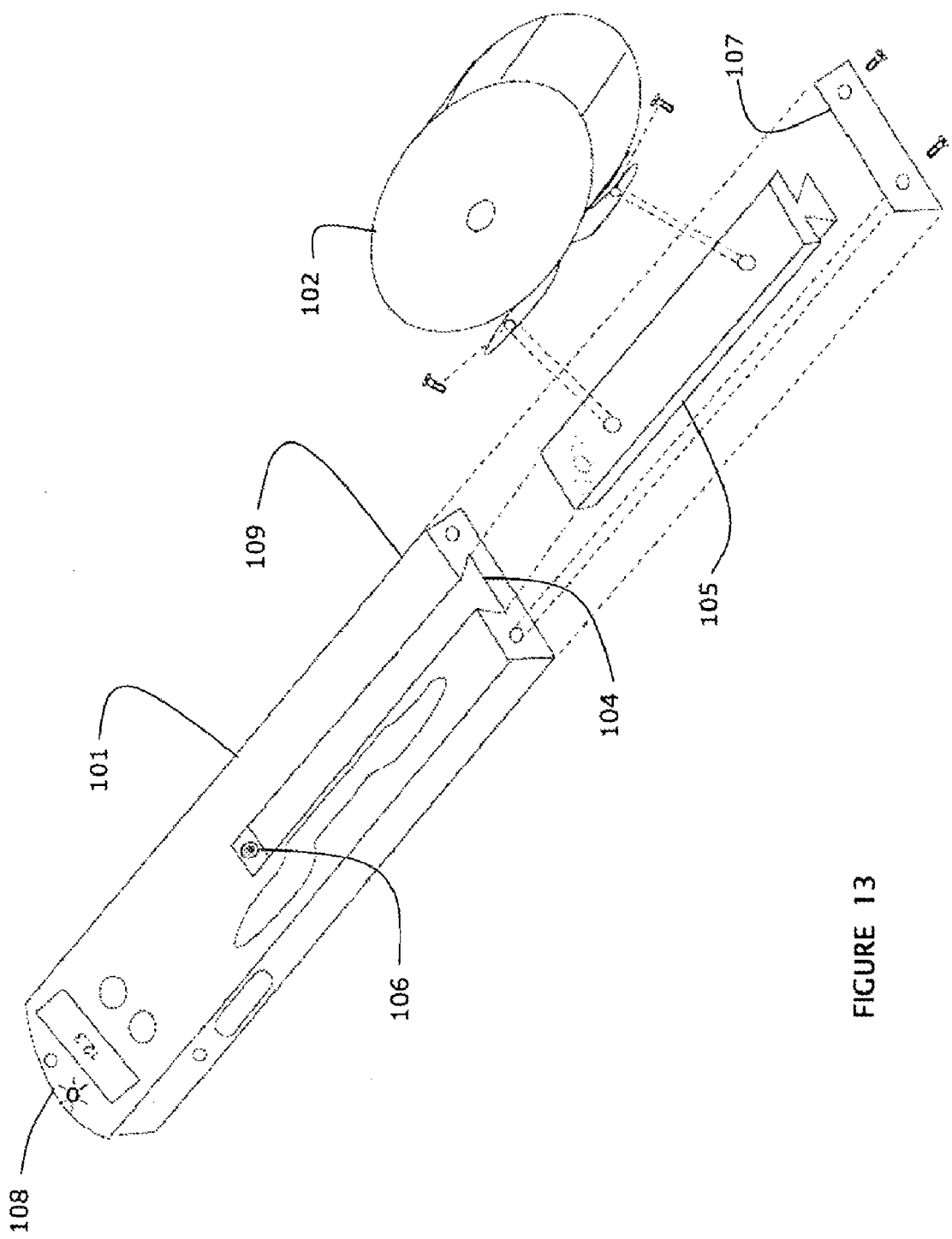
FIG. 13 is an exploded view of a reel and translation stage according to some embodiments of the present invention.

In some embodiments of the present invention, as seen in FIGS. 12 and 13, the line tension measuring device is located in a translation stage 101 which bridges between a fishing reel 102 and a fishing pole 103. The translation stage 101 is adapted to measure and display the force along the pole axis direction, a force which is indicative of the line tension in the fishing line from the reel and running along the pole.

In some embodiments, the translation stage 101 has a main body 109 with a slot 104 adapted to receive a slider 105. The fishing reel 102 mounts to the slider 105 which is a receiving portion of the stage, and this sub-assembly may move within the slot 104, which is part of the mounting portion of the stage. The slider 105 may be constrained within the slot 104 by an end plate 107. The slider 105 may simply slide, or may slide with the aid of bearings or other friction reducing devices in some embodiments.

The slider 105 contacts the pressure sensor 106 which measures the force applied by the fishing line. The fishing line pulls the reel 102 and the slider 105 on to which the reel 102 is mounted into the pressure sensor 106. The signal from the pressure sensor 106 drives the line tension display device 108 through the electronics package within the translation stage. Since the fishing line pulls essentially parallel to the slider 105, the force applied on the pressure sensor 106 is essentially equivalent to the force on the fishing line. The use of the slider allows for the use of a standard fishing pole, and a standard reel, with the enhanced functionalities of the line tension measuring device. The translation stage may use other means for the linear translation of the reel relative to the pole in some embodiments. The line tension display device may be a visual display such as a numeric readout indication of pounds of force.

Figure 14:
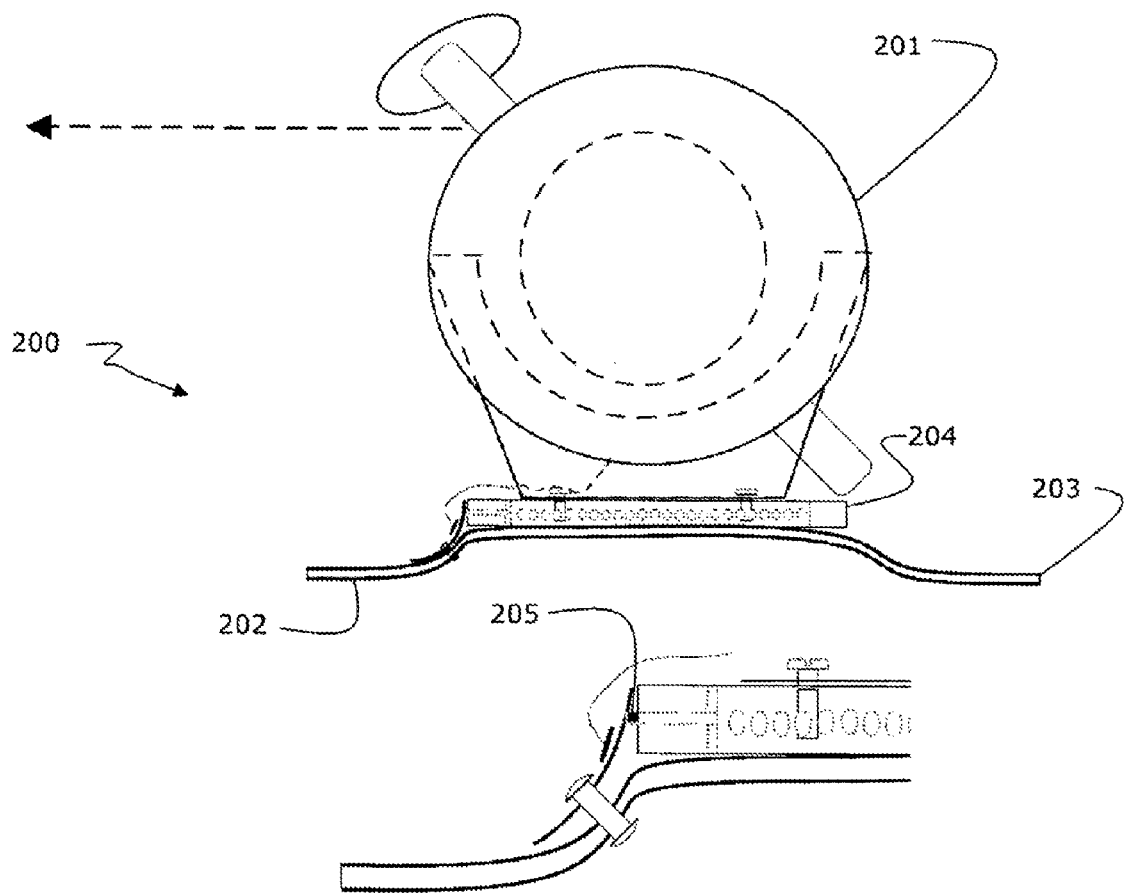
FIG. 14 is a side view of a reel according to some embodiments of the present invention.
Figure 15:
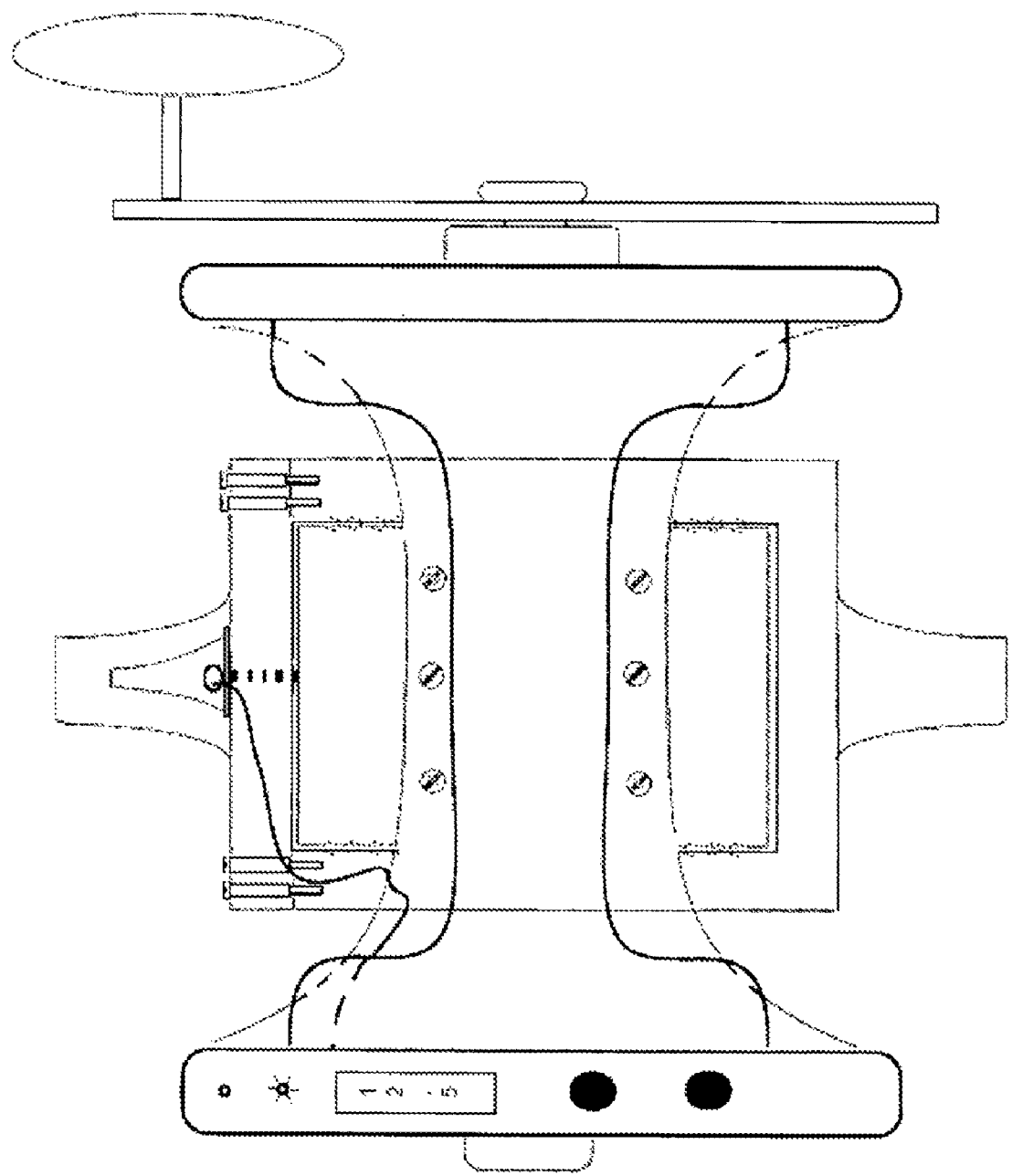
FIG. 15 is a side view of a reel according to some embodiments of the present invention.

In some embodiments of the present invention, as seen in FIGS. 14 and 15, an apparatus 200 includes both a reel body 201 as well as the line tension measuring device 204. The reel 201 has a first tab 202 and a second tab 203 adapted to be inserted into and captured by a standard pole interface. The reel 201 may have a frame for supporting a line spool, wherein the line spool has a spool rotation axis. The measuring device 204 includes a first portion attached to the reel body 201 as well as a second portion which includes the first and second tabs. The first portion and the second portion are adapted to slide relative to each other, using sliding surfaces, bearings, or other means. The first portion presses upon a force gauge 205 which is adapted to measure the force between the two portions, which is a very good representation in the tension in a line from the reel running down the pole.

Figure 16:
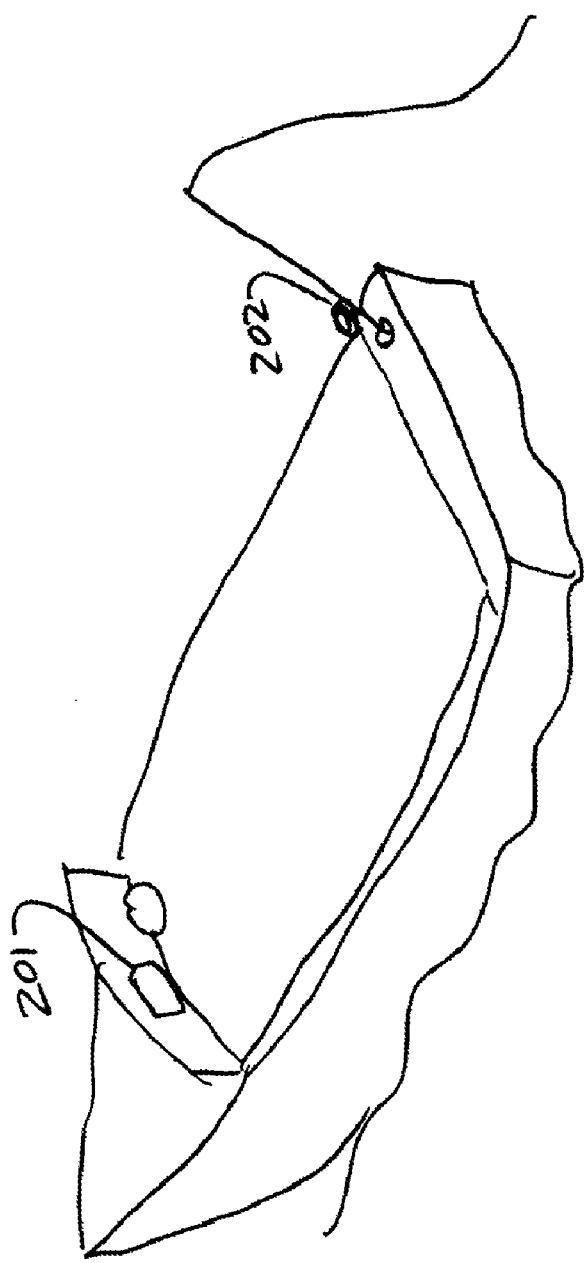
FIG. 16 is a sketch of a line tension measuring device with a wireless transmitter according to some embodiments of the present invention.

In some embodiments of the present invention, as seen in FIG. 16, the line tension display device 201 may be separated from the reel 202, the translation stage, and even the pole. The line tension display device 201 may be connected via wireless transmission to the line tension measuring device. The display may be on the dash of the fishing boat, for example, adjacent to other electronics such as a fish finder. This type of remote use may allow a user to view the line tension of a trolling line while piloting a boat, for example.

While the invention has been particularly shown and described with reference to preferred embodiments thereof, it will be understood by those skilled in the art that various changes in form and details may be made therein without departing from the spirit and scope of the invention.

I claim:

1. A fishing reel seat comprising:
   (a) a reel mounting mechanism having a longitudinal axis configured for firmly attaching a fishing reel, and
   (b) a reel mount receiving portion, wherein said reel mounting mechanism is configured to move in a substantially longitudinal direction with respect to the reel mount receiving portion in response to an externally generated force, and
   (c) a force measurement device comprising a sensor configured to produce a response, in operational mode, indicative of said externally generated force based in the movement of said reel mounting mechanism with respect to said reel mount receiving portion.

2. The fishing reel seat of claim 1 further comprising a visual display configured, when in operational mode, to display a value based on said response of said force measurement device indicative of said externally generated force.

3. The fishing reel seat of claim 1 further comprising an electrical data connection configured to allow external equipment to monitor an output of said force measurement device.

4. The fishing reel seat of claim 1 further comprising a wireless transmitter, said wireless transmitter adapted to transmit an output of said force measurement device.

5. The fishing reel seat of claim 4 further comprising a visual display, said visual display physically separated from said fishing reel seat, wherein said visual display displays a value based upon information transmitted by said wireless transmitter.

* * * * *